(12) United States Patent
Machlinski et al.

(10) Patent No.: US 6,459,079 B1
(45) Date of Patent: Oct. 1, 2002

(54) SHIPBOARD CHEMICAL AGENT MONITOR-PORTABLE (SCAMP)

(75) Inventors: Kevin J. Machlinski, Crofton, MD (US); Michael A. Pompeii, Fredericksburg, VA (US)

(73) Assignee: The United States as represented by the Secretary of the Navy, Washington, DC (US)

( * ) Notice: Subject to any disclaimer, the term of this patent is extended or adjusted under 35 U.S.C. 154(b) by 11 days.

(21) Appl. No.: 09/613,995

(22) Filed: Jul. 11, 2000

(51) Int. Cl.[7] .............................................. H01J 49/40
(52) U.S. Cl. ....................................................... 250/286
(58) Field of Search ................................. 250/286, 287, 250/288

(56) References Cited

U.S. PATENT DOCUMENTS

| | | | |
|---|---|---|---|
| 3,668,382 A | * 6/1972 | Cohen et al. | 250/41.9 TF |
| 4,445,038 A | 4/1984 | Spangler et al. | 250/382 |
| 5,083,019 A | 1/1992 | Spangler | 250/286 |
| 5,162,649 A | * 11/1992 | Burke | 250/287 |
| 5,227,628 A | 7/1993 | Turner | 250/286 |
| 5,300,773 A | 4/1994 | Davies | 250/286 |
| 5,455,417 A | * 10/1995 | Sacristan | 250/287 |
| 5,491,337 A | 2/1996 | Jenkins et al. | 250/287 |
| 5,587,581 A | 12/1996 | Stroosnyder | 250/287 |
| 5,723,861 A | * 3/1998 | Carnahan et al. | 250/287 |
| 5,736,739 A | * 4/1998 | Uber et al. | 250/287 |
| 5,952,652 A | * 9/1999 | Taylor et al. | 250/286 |
| 5,965,882 A | * 10/1999 | Megerle et al. | 250/287 |
| 6,064,070 A | * 5/2000 | Schnurpfeil | 250/423 R |
| 6,239,428 B1 | * 5/2001 | Kunz | 250/287 |

* cited by examiner

Primary Examiner—Kiet T. Nguyen
(74) Attorney, Agent, or Firm—James B. Bechtel, Esq.; Raymond H. J. Powell, Jr., Esq.

(57) ABSTRACT

A portable system for sampling the ambient air of a selected environment for the presence of unwanted chemical warfare vapors, such as nerve or blister gases, is disclosed. The excitation for the electrical elements of the system can be originated from a battery or from an ac excitation. The system comprises a detector unit having first and second ion mobility spectrometers which simultaneously detect and monitor for the presence of the chemical agent vapors so as to provide an accurate and quick determination of the unwanted chemical vapor within the selected environment, without false alarming to non-chemical warfare agent vapors, which act as interferents. The system design also allows monitoring in the presence of electromagnetic interference (EMI).

20 Claims, 5 Drawing Sheets

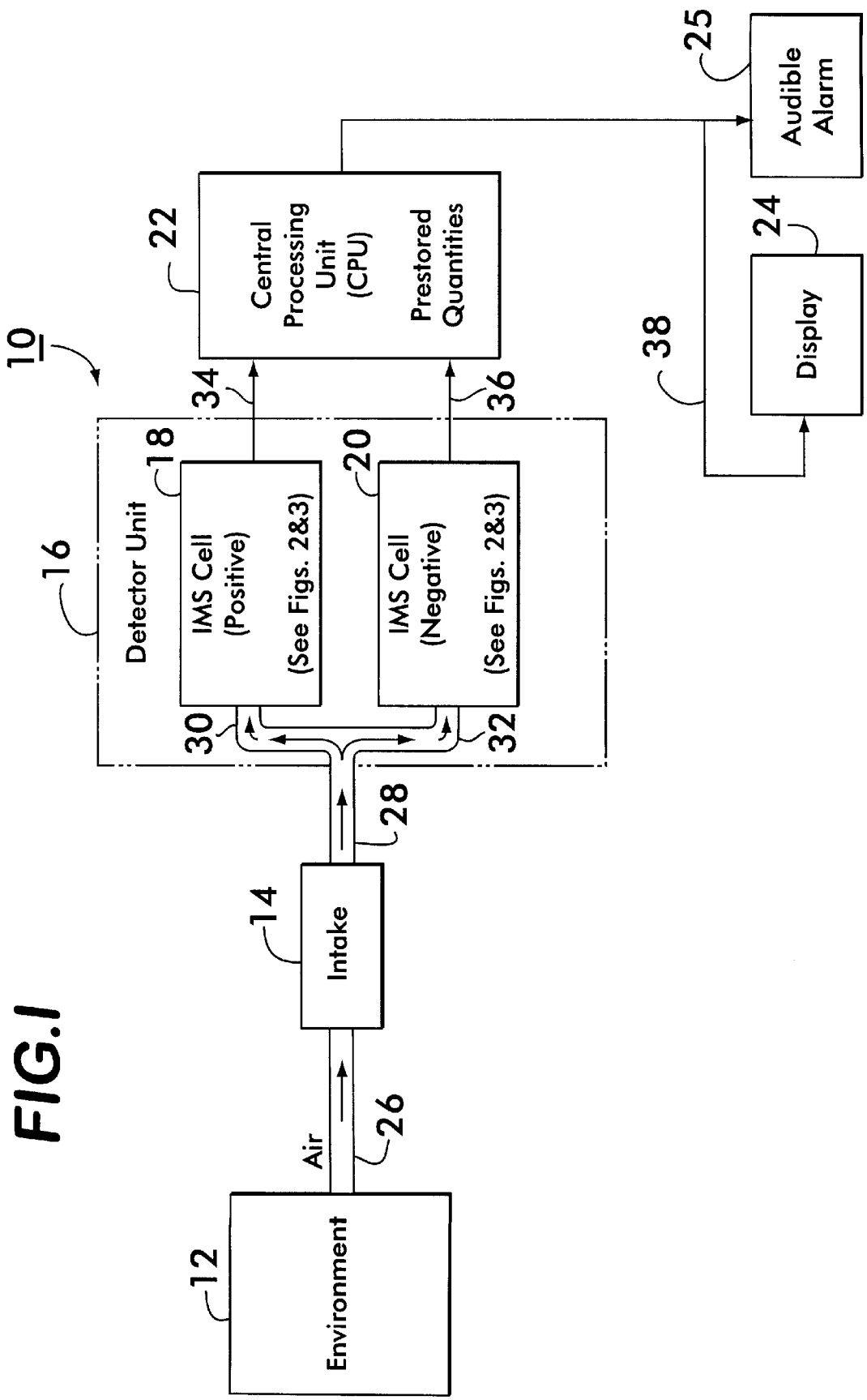

SHIPBOARD CHEMICAL AGENT MONITOR-PORTABLE (SCAMP)

CROSS-REFERENCE TO RELATED APPLICATIONS

This application is related to the invention described in U.S. patent application Ser. No. 90/853,926, and which is filed concurrently herewith.

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

The present invention relates to a system used to analyze compositions to determine what chemical elements are present therein and, more particularly, to a system that analyzes an air sample and, if undesired chemical warfare vapors are present therein, provides signals to activate alarms.

The ambient by which one is surrounded is of utmost importance. However, the ambient may suffer from pollution that allows the surrounding atmosphere to be contaminated, especially by man-made waste and vapor pollutants.

The environment by which one is surrounded may also be invaded by more serious pollutants, especially during terrorist situations or during warfare, in particular, chemical warfare. Chemical warfare involves the use of chemicals, such as blister and nerve gases, that attack humans and animals, with the human suffering severe bodily pain and/or death within minutes of exposure.

Current state of the art portable chemical warfare agent detectors have not demonstrated the capability to function properly on board ship due, in part, to the presence of electromagnetic interference (EMI) and non-chemical warfare (CW) agent vapors which act as interferents. These interferent vapors tend to cause false positive alarms or impede the detection and identification of the chemical warfare vapor.

Systems for measuring samples to determine the contents thereof are known and some of which may employ ion mobility spectrometers (IMSs), such as described in U.S. Pat. No. 4,445,038; 5,083,019; 5,300,773; 5,491,337; and 5,587,581, and all of which are herein incorporated by reference. The IMS provides a quantitative measurement of the contents of the molecules being sampled by measuring a time of "flight" of the ions of the molecules through a drift region of the IMS which is determined by the ion mobility characteristic of the ions being sampled and which, in turn, provides the identity and the concentration of the composition being measured. Accordingly, it is desired that means be provided employing ion mobility spectroscopy technology that analyzes the environment to detect the presence of unwanted chemical warfare agent vapors and provide alarm thereto, but without alarming to common interferents and EMI found in a shipboard environment. More particularly, it is desired that an Ion Mobility Spectrometer (IMS) be provided that yields a quick and improved accurate determination of these unwanted chemical warfare agent vapors so that the environment may be quickly purged thereof.

OBJECTS OF THE INVENTION

It is a primary object of the present invention to provide a system utilizing an IMS that accurately detects and monitors for the presence of undesired chemical warfare agent vapors in an environment. It is also equally important for the system not to alarm in an environment when specific chemical warfare agent vapors are not present.

It is another object of the present invention to provide a system employing an IMS that quickly, yet accurately, detects and monitors for the presence of undesired chemical warfare vapors in an environment and, upon detection thereof, provides an alarm indication.

Another object of the present invention is to provide a system having at least a first and second configuration so that an alarm condition is only generated if there is an agreement between the detection derived separately from the first and second configurations.

In addition, it is an object of the present invention to provide a system employing first and second IMSs to advantageously detect ions having both predominately positive and negative polarities, respectively, so as to simultaneously detect separate gaseous samples having respective positive and negative charge characteristics.

It is another object of the present invention to provide for an instrument that uses ion mobility spectroscopy technology that analyzes molecules of chemical agent vapors by determining the cluster arrangement of the ions making up the chemical vapor agents and conditions the molecules of selected vapors so that these molecules are more easily and accurately detected by an IMS operated to more advantageously detect ions manifesting a positive or negative charge.

Furthermore, it is an object of the present invention to provide for an IMS that generates an electrical signal which is routed to means for comparing the electrical signal against predetermined signals indicative of unwanted and/or dangerous compositions of gaseous vapors, and if a match exists therebetween, an alarm is generated.

In addition, it is an object of the present invention to provide a system that has the ability to operate on standard ship's power or provide rechargeable means so as to operate on battery power making the system portable.

Another object of the present invention is to reduce the weight and size of the associated elements making up the system so as to further contribute to the portability of the system.

SUMMARY OF THE INVENTION

The invention is directed to a system for sampling the ambient of a selected environment for the presence of unwanted, predetermined chemical vapors therein.

The system comprises means for obtaining a sample of the selected environment and means for conditioning the sample into a vapor containing known molecules. The system further comprises means for receiving the vapor comprising ion clusters that define ions of the molecules. The means for receiving comprises first and second ion mobility spectrometers with one of the ion mobility spectrometers having arranged therewith a reagent source. The means for receiving is capable of being powered by a battery. Each of the first and second ion mobility spectrometers provides an electrical signal representative of the respectively received defined ions of the molecules. The system further comprises means for comparing each of the representative electrical signals of the first and second ion mobility spectrometers against predetermined signals representative of predetermined chemical vapors and generating an alarm signal if a match exists therebetween.

BRIEF DESCRIPTION OF THE DRAWINGS

A better understanding of the present invention may be realized when considered in view of the following detailed description, taken in conjunction with the accompanying drawings wherein:

FIG. 1 is a block diagram of the system of the present invention;

FIG. 2A is a schematic of the detector unit of FIG. 1 while

DETAILED DESCRIPTION OF THE PREFERRED EMBODIMENTS

Figure 2A:
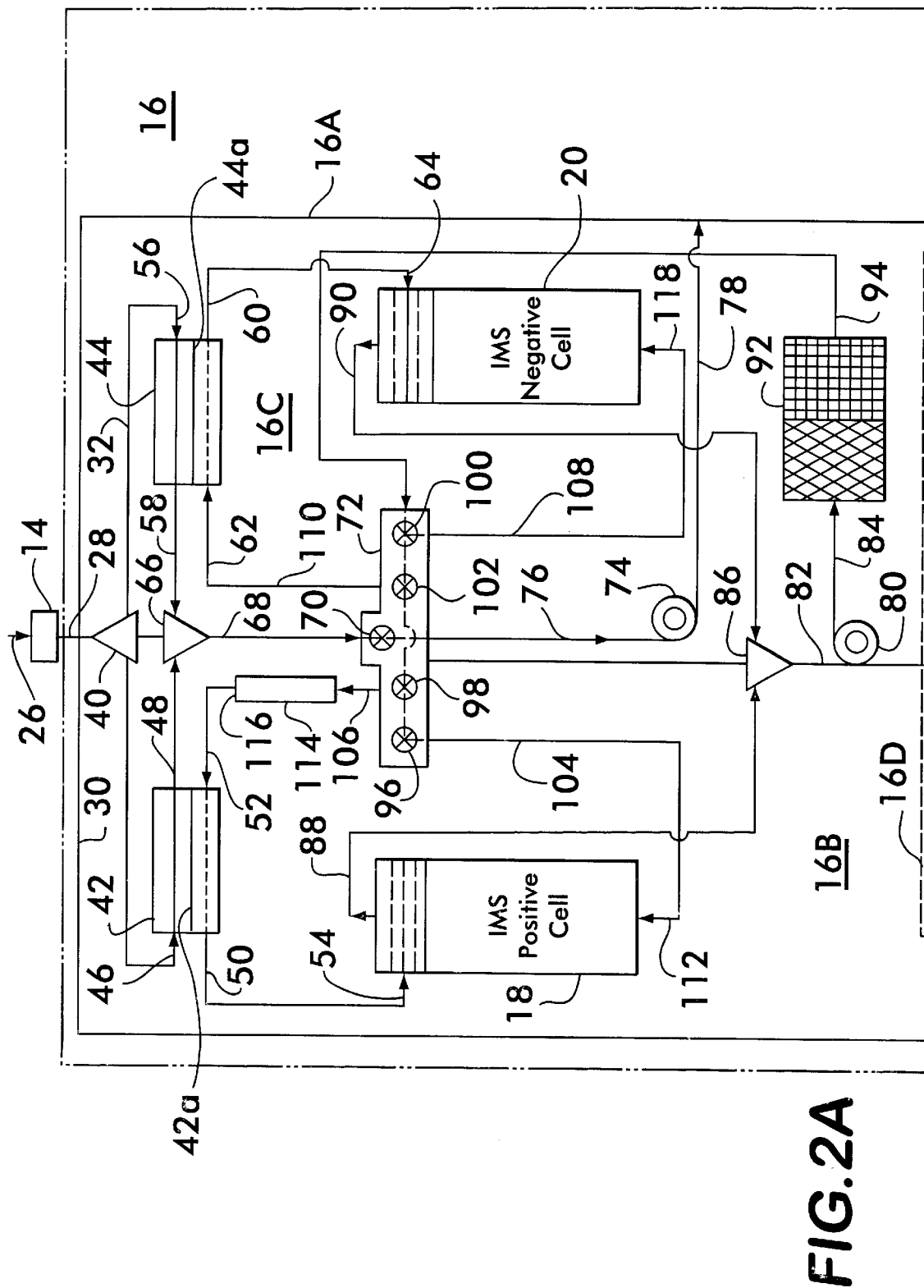

Referring to the drawings, wherein the same reference number indicates the same element throughout, there is shown in FIG. 1 a block diagram of the system 10 of the present invention. The system 10 samples the ambient of a selected environment 12 by means of an intake fitting 14 having an internal filter to remove dust/lint particles, a detector unit 16 comprising an ion mobility spectrometer (IMS) cell (POSITIVE) 18 and an ion mobility spectrometer (IMS) cell (NEGATIVE) 20, a central processing unit (CPU) 22 having pre-stored quantities, and a display 24, as well as an audible alarm 25. In actuality, the intake fitting 14, the central processor unit (CPU) 22 and the display 24 are integral with the detector unit 16.

The detector unit 16 has the ability to operate on standard ship's power or is provided with rechargeable means so as to operate on battery power further contributing to, along with other features of the present invention, making the system 10 portable. The detector unit 16 serves as means for receiving and ionizing the treated vapors into cluster arrangements that define ions of the molecules and as means for receiving the clusters of the defined ions and providing corresponding electrical signals thereof. The CPU 22 serves as the means for comparing the electrical signals generated by the detector unit 16. The CPU 22 has reprogramming capabilities so that the routines running therein may be easily updated to accommodate new/future sampled vapors. The CPU 22 incorporates parallel processors. One processor's sole function is a detection routine, while the other processor runs the system functions, thereby decreasing response time.

The system 10 employs at least one detector unit 16 having at least two ion mobility spectrometers 18 and 20, with the ion mobility spectrometer 18 operating in a mode to detect ions predominately having a positive polarity and operatively cooperating with a reagent source that treat an associated portion of sample being measured so as to be more easily detected by the ion mobility spectrometer 18 operating in the positive mode.

In general, the intake 14 draws air, along flow path 26, which serves as a sample from the selected environment 12. After the intake (with integral filter), the sampled air passes over a semipermeable membrane. The membrane minimizes the introduction of water vapor into the cells 18 and 20 (which are arranged in a closed-loop system). The intake 14 preconditions the sample and delivers the sample on to flow path 28 which, in turn, is delivered to IMS cell 18 via flow path 30 and to IMS cell 20 via flow path 32. The IMS cells 18 and 20 provide electrical signals on signal paths 34 and 36, respectively, that are routed to a central processing unit 22. The central processing unit 22 compares the received signals on signal path 34 and 36 against pre-stored quantities and, if a comparison exists therebetween, provides an electrical signal on signal path 38 that is delivered to display 24. If the comparison fails, the central processing unit 22 delivers via signal path 38 an electrical signal to the audible alarm 25. The pre-stored quantities correspond to electrical signals representative of gaseous vapors of unwanted or dangerous compositions, such as nerve or blister gases used in chemical warfare, or pollutants that can contaminate the environment 12 being monitored.

FIG. 1 illustrates a system 10 referred to herein as Shipboard Chemical Agent Monitor-Portable (SCAMP) comprised of an arrangement of a single detector unit 16 and allows the CPU 22 to generate an error signal upon the detection of an alarm condition therein. The system 10, in particular, the detector unit 16, as will be described, is designed by appropriate means, such as the confinement of associated circuitry onto single circuit boards and into single confined compartments, as well as providing all operating circuit with appropriate protection against electromagnetic interference (EMI) discussed in the "Background" section. This EMI protection provides the system 10 with the capability (lacking in prior art devices) of detecting chemical-warfare (CW) agent vapor in the presence of shipboard EMI. Furthermore, as will be described, the CPU is provided with operating routines, that are detection algorithms, that are designed not to alarm to common shipboard interferents, also discussed in the "Background" section.

In general, each of the ion mobility spectrometer (IMS) cells 18 and 20 accepts ions in a vapor sample, and then separates those ions in an electric field. The acceleration of the ion in an electric field is a function of its charge and mass and, at atmospheric pressure, of its shape and size as well. The characteristics that tell how fast a particular ion can move through an electric field at a given temperature and pressure is called the mobility of the ion, and such is an indication for determining the make up of the molecules of the vapor sample being analyzed and measured by the IMS cells 18 and 20.

At atmospheric pressure, ions and molecules can cluster together in a way unique to the molecule producing the ions. This clustering does not need to be with similar molecules. These non-similar molecules are called reagents. As used herein, G-agent vapor molecules cluster with acetone molecules, forming positively charged cluster ions. As further used herein, H-agent vapor molecules cluster with hydroxyl ions to form negatively charged cluster ions. Further, as used herein, a single-agent ion clustered with reagent molecules is called a monomer. Further still, as used herein, a two- and a three-agent molecule clustered with reagent molecules is called a dimmer and a trimmer, respectively.

In the separation method of the IMS cells 18 and 20 to be further discussed with reference to FIG. 3, the ions start from rest at the same time and travel a known distance along a drift region having a high-voltage gradient which is applied thereto. A cathode electrode is located at the end of the drift region in each IMS cells 18 and 20 to detect the traveling ions. The smaller ion clusters have greater mobility and reach the end of the drift region first, as compared to other clusters. Heavier clusters arrive later at the cathode electrode, and their arrival time is on the order of their mass. The ion mobility is sometimes referred to as determining the time of "flight" as more fully disclosed in the previously incorporated by reference U.S. Pat. No. 5,587,581 (hereinafter the '581 patent). As used herein, the arrival time at the cathode electrode is primarily a measure of the size and shape of the cluster ions.

Each substance or composition operated on by each IMS cells 18 and 20 that can be ionized produces a unique electrical IMS signal. As will be further described with reference to the CPU 22, an unknown substance can be identified by comparing its unique IMS signal, also called its IMS signature, with a set of previously recorded signatures of known substances making up a reference library. The waveforms of the IMS may have peaks that represent information regarding the identity and concentration oft he samples being measured in a manner more fully described in the '581 patent. The reference library may be made up to identify any substance at any concentration thereof with such substances being, for example, nerve or blister gases. If the unknown substance IMS signature matches one of the known signatures in the reference library, that unknown substance is identified.

The overall fluid flow of system 10 may be further described with reference to FIG. 2A.

Figure 2B:
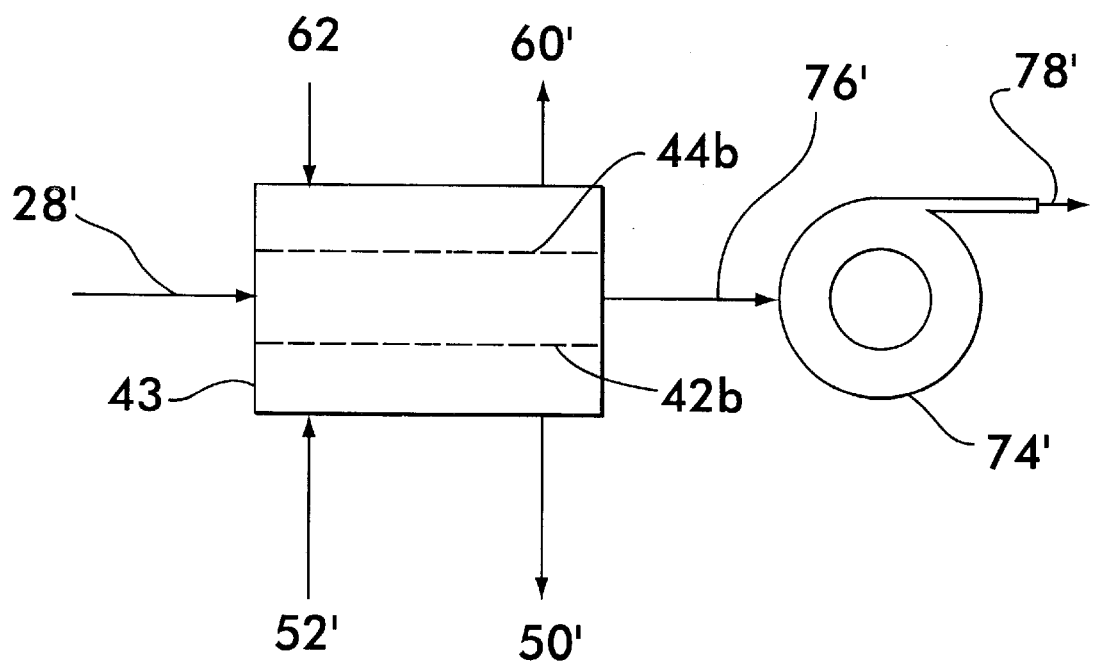
FIG. 2B illustrates an alternative arrangement of selected elements of FIG. 2A.

As seen in FIG. 2A, the fluid flow on path 28 having a first flow rate of 2.0 LPM, first encounters a manifold 40 that serves as a dividing means that receives the sample at the first flow rate and separates the sample flowing at the first flow rate into first and second paths 30 and 32, respectively, (also shown in FIG. 1) having second and third flow rates which are equal to one-half of the first flow rate. More particularly, the dividing means 40 divides the fluid flow on path 28 into two paths 30 and 32, each having a preferred positive and negative flow rate of 1.00 LPM which are respectively directed into membrane retainers 42 and 44, respectively, containing, semipermeable membranes 42a and 44a. The flow rate of 1.00 LPM is shown in FIG. 3, for the sake of clarity, as being directed into two membrane retainers 42 and 44, but in actuality, the retainers 42 and 44, along with their membranes, advantageously can be a one piece retainer, again for the sake of reducing weight and increasing the portability of the system 10, as illustrated in FIG. 2B. In FIG. 2B, a single retainer 43 supporting semipermeable membranes 42b and 44b divide the retainer 43 into three chambers, the center chamber passing the sample gas at the first flow rate, which is drawn through the retainer 43 by pump 74'. It will be appreciated that the ports 50', 52', 60', 62'in FIG. 2B correspond to ports 50, 52, 60, and 62 in FIG. 2A.

Referring again to FIG. 2A, the retainer 42 has first, second, third and fourth ports 46, 48, 50, and 52, respectively, with the first port 46 having fluid communication with the second flow rate 30 and the second port 48 accepting the fluid flow that does not migrate through the membrane in retainer 42. The third port 50 is fluidly coupled to a port 54 of the IMS cell 18. The second retainer 44 has first, second, third and fourth ports 56, 58, 60, and 62, respectively, which are fluidly coupled in a manner similar to those of retainer 42. The port 60 of retainer 44 is fluidly connected to port 64 of the IMS cell 20.

Each of the retainers 42 and 44, as previously discussed, is merged into a single retainer, which is preferably comprised of stainless steel and has a mount that holds a 1.0 mi-thick semipermeable membrane of a dimethyl silicone/polycarbonate hybrid material. The semipermeable membranes within the retainers 42 and 44 serve as means to selectively allow sample molecules of interest, such as those contained in nerve or blister gases or other pollutants contained in the sample being measured, into the IMS cells 18 and 20, while excluding excess water therefrom. As the air sample passes over each of the semipermeable membranes, a few sample air molecules migrate through the semipermeable membranes and get entrained in the recirculating air flows (to be described) of the detector unit 16. The few sample air sample molecules that pass through the semi-permeable membranes are the only part of the original ambient air sample that actually get analyzed by the IMS cells 18 and 20.

The port 48 of retainer 42 and the port 58 of retainer 44 are fluidly coupled to a manifold 66 which, in turn, provides an output of fluid path 68 that is fluidly coupled to a port 70 of a metering manifold 72. The output of port 70 is fluidly coupled to a sample pump 74 by way of fluid path 76. The sample pump provides an output on fluid path 78 which is exhausted from the detector unit 16.

The detector unit 16 further comprises recirculation means comprising a recirculating pump 80 having an input 82 and an output 84. The input 82 is fluidly coupled, via a manifold 86, to an air recirculation port 88 of the IMS cell 18 and also to an air recirculation port 90 of the IMS cell 20.

The output 84 of the recirculation pump 80 is fluidly connected to a cartridge 92 having an input and an output 94 and containing a desiccant.

The desiccant cartridge 92 is interposed in the recirculating air of the detector unit 16 so as to clean and dry the recirculating air. Care should be exercised in the selection of the size of the desiccant cartridge 92 so as to keep it as small as feasible, thereby further contributing to the portability of the system 10. The recirculating air of the detector unit 16 includes desiccant cartridge 92 that filters out all of the contaminates from the reduced air, that is, the sample air which permeates through the membrane of the second and third flow rates on paths 30 and 32, respectively. The desiccant cartridge 92 may be filled with a molecular sieve material (size 4A) and a charcoal (untreated 6×16 mesh wire) which may be a BPL type, known in the art. The molecular sieve material removes residual water vapor and the BPL charcoal removes any organic contaminants.

During operation, the desiccant cartridge 92 may typically become slowly loaded with contaminants and become unable, over a period of time, to maintain a clean and dry environment inside the recirculating air circuit of the detector unit 16 and, thus, desiring replacement thereof. The average life of the desiccant cartridge 92 is approximately 500 operating hours.

The output 94, having a flow rate of approximately 2.4 LPM, of the desiccant cartridge 92 is routed to second dividing means comprising the metering manifold 72. The second dividing means 72 is a series of flow valves 96, 98, 100 and 102 that separates the output 94 of desiccant cartridge 92 into first 104, second 106, third 108, and fourth 110 flow paths, respectively carrying forth, fifth, sixth and seventh flow rates. The first and second flow paths 104 and 106, which are routed to the positive IMS cell 18, separate the output 94 of the desiccant cartridge 92 into fourth and fifth flow rates, wherein the fourth flow rate is greater than that of the fifth flow rate. More particularly, it is preferred that the fourth flow rate be approximately 0.7 LPM, whereas the fifth flow rate is preferred to be approximately 0.25 LPM. The sixth flow rate is preferred to be approximately 1.2 LPM, whereas the seventh flow rate is preferred to be approximately 0.25 LPM. The sample flowing at the fourth flow rate is routed, via flow path 104, to port 112 of the IMS 18, whereas the fifth flow rate is routed, via flow path 106, to a reagent source 114 having an input port and an output port 116. The sample flowing at the sixth flow rate is routed, via flow path 108, to port 118 of the IMS 20, whereas the sample flowing at the seventh flow rate is routed, via flow path 110, to port 62 of the second retainer 44.

The reagent source 114 may be an acetone vapor source consisting of a Teflon diffusion tube immersed in liquid acetone contained in a stainless steel vessel that is mounted next to the positive IMS cell 18. The output 116 of the reagent source 114 is routed to the port 52 of the retainer 42. In operation, just prior to entering the positive IMS cell 18, the recirculating air within the detector unit 16 passes through the immersed tube of the reagent source 114 and the acetone molecules therein diffuse into the tube and mix with the recirculating air at a constant rate of approximately 5000 ng/min at 60° C. The acetone molecules increase the positive polarity of the ions of the molecules being measured by the IMS cell 18 and, thus, increase the sensitivity of the positive IMS cell 18 operated in a manner to be further described with reference to FIG. 3.

A separate reagent vapor source similar to the reagent vapor source 114 is not required for the negative IMS cell 20. A small amount of residual atmospheric water vapor migrates through the semipermeable membrane of retainer 44 with the sample vapor and enters, by way of port 60 of the retainer 44 and fluid path 64, the ionization chamber of the IMS cell 20, to be described. These water molecules act as the reagent for the negative polarity ion reactions within the IMS cell 20 and, thus, negate the need for a separate reagent vapor source 114 for IMS cell 20.

The components comprising the IMS cell 18 are preferably placed into a compartment 16B and, similarly, the components comprising IMS cell 20 are also preferably placed into a compartment 16C with both compartments being located in a single housing 16A. The single housing 16A is provided with appropriate electromagnetic interference (EMI) protection so that the system 10, in particular, the IMS cells 18 and 20 successfully detect chemical warfare (CW) agent vapor in the presence of shipboard electromagnetic interference (EMI). The single housing 16A has a heater 16D operatively disposed in the single housing. Preferably, the heater 16D is operated so as to maintain the temperature of the IMS cells 18 and 20 at a constant temperature of about 180° F. The heater advantageously can be either a 163 watt strip heater (AC) and/or 21 watt strip heater (DC) mounted under the cells 18 and 20 so as to maintain their temperature and heat their surrounding components in order to prevent sample vapor from condensing as it travels through the detector unit 16.

The IMS cells 18 and 20 may be further described with reference to FIG. 3, which is a schematic that is generically applicable to both the IMS cells 18 and 20, even though the IMS cell 18 predominately operates with positive potentials and the IMS cell 20 predominantly operates with negative potentials. The descriptions of the IMS cells 18 and 20 with reference to FIG. 3 are generic, but point out, as needed, the differences in the operation of the IMS cells 18 and 20.

Figure 3A:
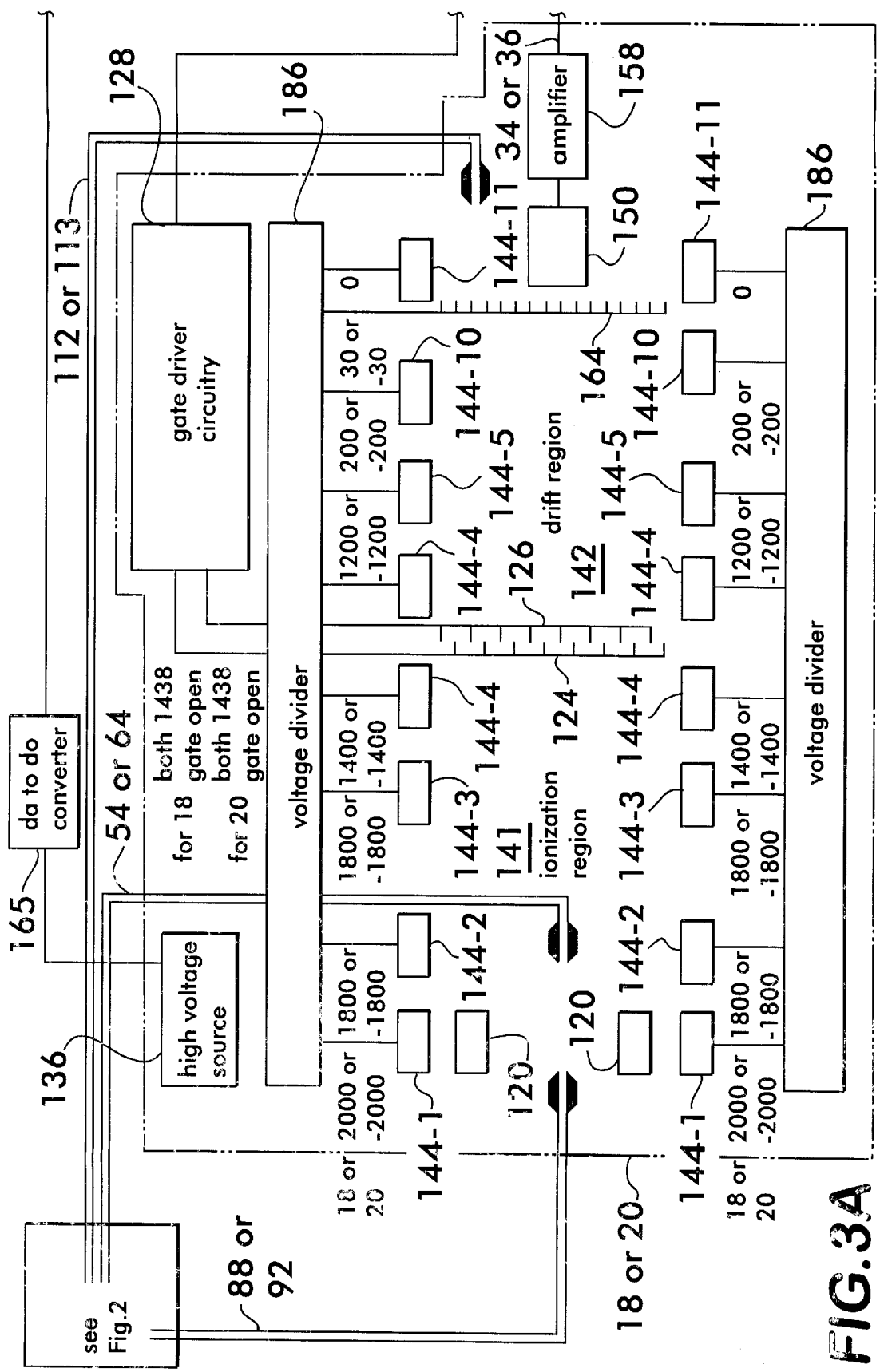
FIG. 3 is a schematic of the IMS cells of FIG. 1.
Figure 3B:
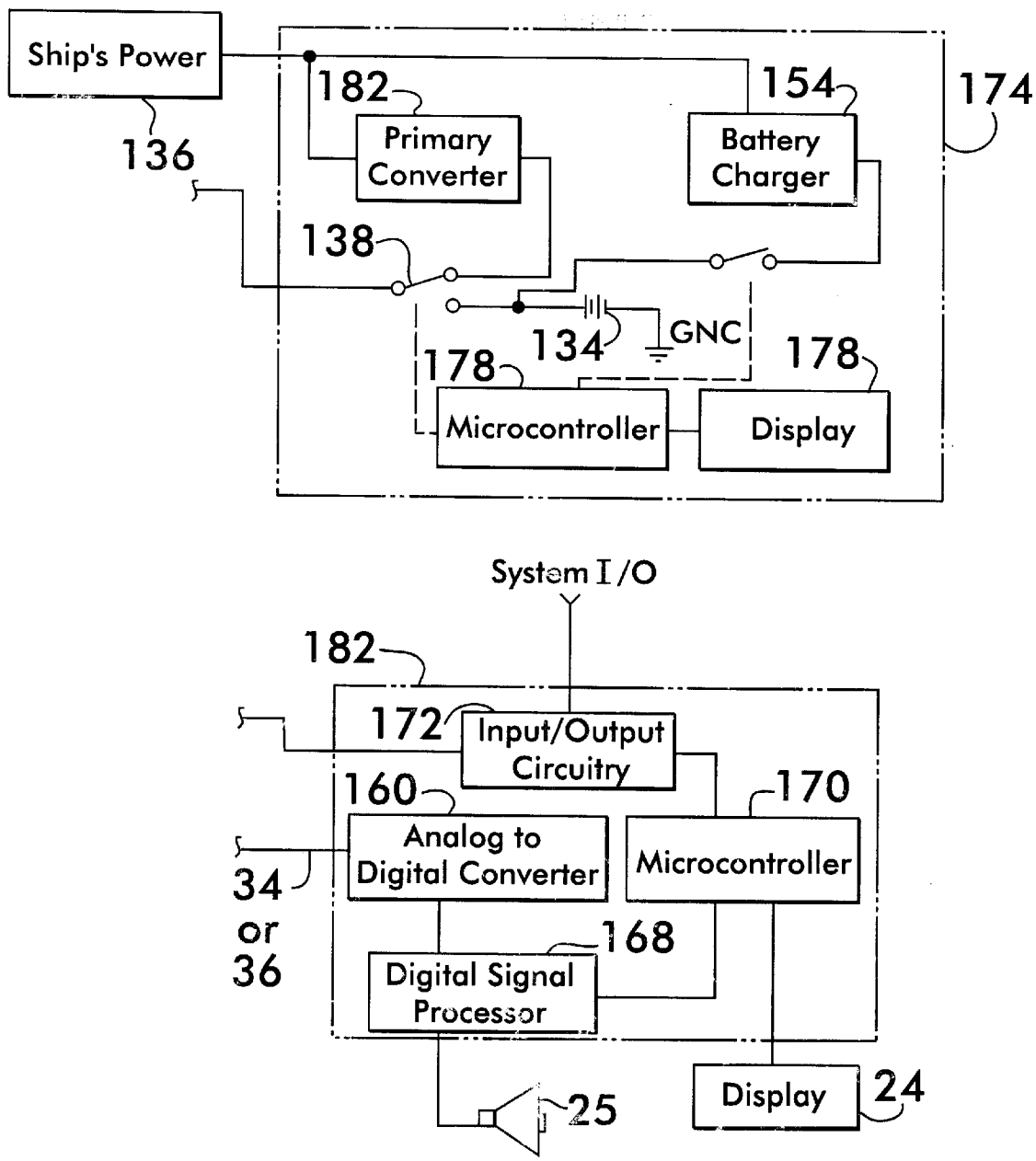

FIG. 3 illustrates an ionization chamber outlined in phantom, which can represent either of IMS cell 18 or 20. IMS cell 18 is referred to as the first ionization chamber; IMS cell 20 is referred to as the second ionization chamber. The use of this first and second terminology to refer to the IMS cells 18 and 20 respectively is maintained throughout. The first IMS cell contains ports 54, 88, and 112, whereas the second IMS cell includes ports 64, 90 and 118, all of which were previously 10 described with reference to FIG. 2.

Each IMS cell is composed of 11 conducting rings 144-1 . . . 144-11 carrying gradually increasing or decreasing voltages, a radioactive source 120, which lines the inside of the first ring 144-1, a shutter grid or gate 122 which resides in the middle of the fourth ring 144-4, an aperture grid 164 (also known as pole guard) and a collector 150. The conducting rings 144-1 . . . 144-11 are insulated from one another as well as from the gate 122, aperture grid 164 and collector 150. The region on the side of the gate 122 including the radioactive source 120 may be thought as the ionization region 141, and the region on the collector 150 side of the gate 122 may be thought of as the 142.

The radioactive source 120 is preferably a foil containing 100 microcuries of Americium—241 which emits beta particles that collide with the mixture of the sample and reagent molecules. The reagent molecules of IMS cell 18 are acetone molecules from reagent source 114, whereas previously discussed, the reagent molecules of IMS cell 20 are from residual water vapor in the system. The beta particles ionize the reagent molecules, and the reagent ions react with the sample molecules, causing the formation of sample molecule ion clusters. The ion clusters formed in IMS cell 18 are positive ion clusters, whereas the ion clusters formed in IMS cell 20 are negative ion clusters.

In the positive cell 18, the 11 conducting rings 144-1 . . . 144-11 are connected to a high voltage source 130 through a voltage divider 186 so that voltage sequentially and evenly decreases from 2000 Volts (V) at the ring 144-1 holding the radioactive source 120 to ground at the ring 144-11 holding the collector 150 in approximately 200 V decrements to provide a negative voltage gradient in the positive IMS cell 18. The grounded ring 144-11, which holds the collector 150, is electrically insulated from the collector 150. When the gate 122 is opened as described hereinafter, the positive ion clusters formed in the ionization region are swept down the gradient through the drift region 142, through the pole guard 164 to the collector 150, which causes a current pulse in the collector 150. The current into the collector 150 is converted to a voltage and amplified by a circuit 158 attached to the IMS cell 18. The time between the gate opening and the arrival of current pulses is proportional to the time required for the ion clusters to move through the drift region. The time to move through the drift region in the presence of an electric field is proportional to the reduced ion mobility which is a characteristic of the particular ion cluster involved. The pattern of pulses which occurs from the time the gate 122 is opened can be used as a signature to identify a substance. The voltage on signal path 34 from the amplifier 158 is digitized by one channel of the analog-to-digital converter 160 on the processor board 162 so the digital signal processor 168 can use the pattern for substance identification.

In the negative cell 20, the 11 conducting rings 144-1 . . . 144-11 are connected to a high voltage source 130 through a voltage divider 186 so that voltage sequentially and evenly increases from −2000 V at the ring 144-1 holding the radioactive source 120 to ground at the ring 144-11 holding the collector 150 in approximately 200 V increments to provide a positive voltage gradient in the negative IMS cell 20. The grounded ring 144-11, which holds the collector 150, is electrically insulated from the collector 150. When the gate 122 is opened as described hereinafter, the negative ion clusters formed in the ionization region 141 are swept up the gradient through the drift region 142, through the pole guard 164 to the collector 150, which causes a current pulse in the collector 150. The current into the collector 150 is converted to a voltage and amplified by a circuit 158 attached to the cell assembly 20. The time between the gate 122 opening and the arrival of current pulses is proportional to the time required for the ion clusters to move through the drift region 142. The time to move through the drift region in the presence of an electric field is proportional to the reduced ion mobility which is a characteristic of the particular ion cluster involved. The pattern of pulses that occurs from the time the gate 122 is opened can be used as a signature to identify a substance. The voltage on signal path 36 from the amplifier 158 is digitized by one channel of the analog-to-digital converter 160 on the processor board 162 so the digital signal processor 168 can use the pattern for substance identification. Information from both the positive cell signature on signal path 34 and the negative cell signature on signal path 36 can be combined as well to identify a substance.

The positive gate assembly 122 is a two wire grid 124, 126 in the same plane placed in the middle of the fourth ring 144-4, which is actuality a two-piece ring with the same high voltage on each of the pieces. The wires alternate so that adjacent wires in the plane belong to different grids. Voltages derived front the same high voltage source 130 that is used by the rings 144-1 . . . 144-11 are applied to the wire grids 124 and 126. These high voltages are somewhat higher than the high voltage on the fourth ring. When the gate 122 is closed, the voltage on one grid 124 is 24v higher than the high voltage on the other grid 126 so that an electric field is produced between adjacent wires in the plane. This transverse field sweeps ions to the more negative wires on the grid 126 where they are neutralized and, thus, resist the movement of the ion clusters into the drift region 142. When the gate 122 is opened, the wire grids 124 and 126 are shorted together, removing the transverse field and allowing the ion clusters to move into the drift region 142 where they are swept down the voltage gradient to the collector 150.

The negative gate assembly 122 is identically constructed as the positive gate assembly and similarly placed in the middle of the fourth ring 144-4 in the negative IMS cell 20. The fourth ring 144-4 in the negative cell 20 is similarly a split ring with same highly negative voltage applied to both sides of the split ring 144-4. Voltages derived from the same high voltage source 130 as the rings 144-1 . . . 144-11 are, applied to the wire grids 124 and 126. These highly negative voltages are somewhat more negative than the highly negative voltage on the fourth ring 144-4 when the gate 122 is closed, the voltage on one grid 124 is 24v more negative than the highly negative voltage on the other grid 126 so that an electric field is produced between adjacent wires in the plane. This transverse field sweeps ions to the less negative wires in the grid 126 where they are neutralized and thus resist the movement of the ion clusters into the drift region 142. When the gate 122 is opened, the wire grids 124 and 126 are shorted together, removing the transverse field and allowing the negative ion clusters to move into the drift region where they are swept up the voltage gradient to the collector 150.

The aperture grid, i.e., pole guard, 164 is another wire grid in which all the wires are at the same voltage and that voltage is approximately 30 V above the ground potential on the ring 144-11 holding the collector 150 in the positive IMS cell 18. The pole guard 164 has a focusing effect which causes pulses to be more narrow and improves the resolution of the IMS cell 18. The pole guard 164 in the negative IMS cell 20 performs the same function but is at a voltage that is approximately 30 V below the ground potential on the ring 144-11 holding the collector 150.

The processor board 162 contains a microcontroller 170 and a digital signal processor (DSP) 168 running in parallel. The microcontroller 162 and associated input output circuitry 172 handle all detector input and output including that of signal controlling the alarm visual display 24, whereas the digital signal processor 168 and associated analog-to-digital converter circuitry 160 handle alarm detection. The digital signal processor 168 also provides an output that controls the audible alarm 25. The use of parallelism between the processors 168 and 170 as well as within the digital signal processor 168 itself reduces the time to alarm. The high degree of circuit integration within the two (2) processors 168 and 170 allows the incorporation of all electronics except the high voltage source 130, amplifier circuitry 158, and DC to DC converter 166 onto a single board 162, reducing the size of the system and contributing to its portability.

The processor board 162, high voltage sources 130, amplifiers 158, pumps, heaters and transducers are powered by DC to DC converter 166 preferably located in detector unit 16. The power for these converters comes from a power management system 174 that can select between a rechargeable battery 134 or ship's power 136 using automatic electronic switching 138 controlled by a microcontroller 178. The power management system 174 also contains a battery charger 180 and can recharge the battery 134 while powering the detector unit 16 from ship's power 136 through the primary converter 182. The power management system 174 contains a display 176 to inform the operator of pertinent information concerning the battery state and power system state in general. The use of the rechargeable battery 134 allows the system 10 to be portable.

OPERATION OF THE SYSTEM OF THE PREFERRED EMBODIMENT

In operation and with first reference to FIG. 2, the detector unit 16 receives the sample air flow at a first rate of 2.0 LPM which is then split between the positive and the negative IMS cells 18 and 20 via the flow paths 30 and 32, respectively. The sample first flow rate is directed into the retainers 42 and 44 and directed across semipermeable membranes in the retainers 42 and 44. A few of the molecules of the sample migrate through the semipermeable membranes and are entrained in the circulating air flow of the detector unit 16. The remaining sample air is directed to the metering manifold 72 via ports 48 and 58 of retainers 42 and 44, respectively, then is immediately exhausted out of the system by way of port 70 of the metering manifold 72 and the sample pump 74.

The detector unit 16 has a recirculating air path formed essentially by recirculating pump 80 and the metering manifold 72. The recirculating pump 80 provides a recirculating air flow of 2.4 LPM which is provided so as to maintain a clean and dry condition inside each IMS cell 18 and 20. The recirculating air is routed through the desiccant cartridge 92 containing a 50% molecular sieve material and a 50% activated BPL charcoal to remove any contaminants from the recirculating air flow.

The acetone vapor reagent source 114 is included in the recirculating air flow circuit of the positive IMS cell 18. This vapor reagent source 114 provides a trace amount the reagent molecules required for the reaction with the G-agent vapor molecules to form the positive ions predominant in the operation of the positive IMS cell 18. The negative IMS cell 20 does not need a separate vapor reagent source similar to the reagent vapor source 114 because there is enough residual water molecules in the air to form hydroxyl ions (negative ions) needed to react with the H-agent molecules predominant in the operation of the negative IMS cell 20.

The two IMS cells 18 and 20 are provided, which is of importance to the present invention, so that IMS cells 18 and 20 operate simultaneously, one in the positive mode and the other in the negative mode. This allows the system 10 to continuously detect both nerve (IMS cell 18) and blister (IMS cell 20) agent vapors.

The sample molecules that migrate through the semipermeable membranes, located in the retainers 42 and 44, become entrained in the recirculating air that contains the reagent vapor molecules. This sample-reagent vapor mixture enters the ionization region 141 (shown in FIG. 3 for both IMS cells 18 and 20). The ionization region 141 for each IMS cell 18 and 20 is surrounded by the radioactive source 120, which gives off beta particles that collide with the associated mixture of the sample-reagent molecules. The reagent molecules ionize and react with the sample molecules to create ion clusters for the molecules thereof.

The gate 122 of each of the IMS cells 18 and 20 is arranged so as to set up an electric field that prevents the ion clusters within the ionization region 141 from passing through into the drift region 142. However, every 30 millisecond interval, the grids 124 and 126, which make up the gate 122, are shorted together. This momentarily removes the potential difference between grids 124 and 126, and eliminates the electric field between them. This "opens" the gate 122 and a small, discrete group of ion clusters enter the drift region 142.

As the ion clusters travel through the length of the drift region 142, the ion clusters separate due to their different ion mobilities in the electric field and arrive at the collector 150 at different times, i.e., the smaller ion clusters have greater mobility and reach the collector 150 ahead of the heavier clusters. As the ion clusters impact on the collector 150, they discharge and create a small ion current. This ion current is made available at the output of the collector 150 in the form of a signal which is amplified by amplifier 158 located in each IMS cells 18 and 20 and converted to a digital voltage by the A/D converter 160. This digital voltage at the output of A/D converter 160 serves as an IMS signature of the sample vapor being measured by each of the IMS cells 18 and 20. These IMS signatures are then analyzed by the application routines running in the CPU 22, e.g., DSP 168 and microprocessor 170.

The CPU 22 advantageously may contain a DSP Chip having routines that analyze digital signals. More particularly, the application programs running in the CPU 22 operate in conjunction with pre-stored quantities, each indicative of a signature of a vapor of interest, such as a vapor that may be created by either of the nerve or blister gas. The CPU 22 compares the IMS signatures present on signal paths 34 and 36 (IMS cells 18 and 20, respectively) with the pre-stored quantities, and if a match exists therebetween, generates an alarm signal via signal path 38 which notifies the operator of the undesired condition. As previously mentioned, the CPU 22 may be easily reprogrammed so as to upgrade the routines to detect new/future vapor agents.

The system 10 may be calibrated by placing a confidence sample in the path of the intake fitting 14 so that its content is analyzed by the system 10. More particularly, the confidence sample may be used to create one or more IMS signatures on signal paths 34 and 36 of FIG. 2, which may be or may not be recognized by the application routines running in the CPU 22 so that a calibration check is generated, which is indicative that the associated elements of the system 10 are operating correctly. This confidence sample, along with the detection algorithms embodied in the operating routines running in the CPU 22, ensures that the system 10 does not alarm to common shipboard interferents.

It should now be appreciated that the present invention provides for an improved detection system that samples the ambient of an environment and detects and monitors for the presence of unwanted chemical agent vapors. The detector unit uses two different ion mobility spectrometers (IMSs) to analyze the air sample and, if unwanted chemical vapors are detected, provides appropriate signals to activate visual displays.

Although the invention has been described relative to the specific embodiments thereof, there are numerous variations and modifications that will become readily apparent to those skilled in the art in the light of the above teaching. It is, therefore, to be understood that, within the scope of the appended claims, the invention may be practiced other than as specifically described.

What is claimed is:

1. A portable system for sampling the ambient of a selected environment for the presence of predetermined chemical vapors therein, said portable system comprising:
    a housing in which are disposed:
    (a) means for obtaining a sample of said selected environment;
    (b) means for conditioning said obtained sample into a vapor containing known molecules;
    (c) means for receiving and ionizing said vapor into clusters that define ions of said molecules, said means comprising first and second ion mobility spectrometers, with only one of said ion mobility spectrometers having arranged therewith a reagent source, each of said first and second ion motility spectrometers providing an electrical signal representative of the respective received defined ions of said molecules;
    (d) means for comparing each of said representative electrical signals of said first and second ion mobility spectrometers against predetermined signals representative of said predetermined chemical vapors and generating an alarm signal if a match exists therebetween; and
    (e) power source means for supplying electrical power to said vapor receiving means capable of being excited by a battery.

2. The portable system according to claim 1, wherein the portable system includes electromagnetic interference protection so as to permit detection of said predetermined chemical vapors in the presence of electromagnetic interference.

3. The portable system according to claim 1, wherein said portable system can be calibrated with respect to known chemical vapors so as to prevent the generation of said alarm in the presence of known interferents.

4. A portable system enclosed in a unitary housing for sampling the ambient of a selected environment for the presence of predetermined chemical vapors therein, said system comprising:
    (a) means for obtaining a sample of said selected environment;
    (b) means for conditioning said obtained sample into a vapor containing known molecules;
    (c) means for receiving and ionizing said vapor into clusters that define ions of said molecules, said vapor receiving means comprising first and second ion mobility spectrometers, with one of said ion mobility spectrometers having arranged therewith a reagent source, each of said first and second ion motility spectrometers providing an electrical signal representative of the respective received defined ions of said molecules;
    (d) means for comparing each of said representative electrical signals of said first and second ion mobility spectrometers against predetermined signals representative of said predetermined chemical vapors and generating an alarm signal if a match exists therebetween; and (e) power source means for supplying electrical power to said vapor receiving means capable of being excited by a battery, wherein said vapor receiving means has respective input ports and an output port for each ion mobility spectrometer; and said means for conditioning said sample comprises:

(a) first dividing means receiving said sample at a first flow rate for dividing said sample at said first flow rate into first and second samples in first and second paths respectively having substantially equal second and third flow rates;

(b) first and second permeable membranes arranged in respective first and second retainers each of which intercepts a respective one of the first and second samples and each of which has first, second, third and fourth ports, with the first port of said first retainer having fluid communication with said second path of said first dividing means, the first port of said second retainer having fluid communication with said third path of said first dividing means, and the respective second port of said first and second retainers exhausting the flow of said first and second samples that do not pass through a respective one of said permeable membranes, said third and fourth ports of each of the first and second retainers being output and input ports respectively with the third port making available the flow of said sample that does pass through a respective one of said permeable membranes; and (c) recirculating means comprising:

(i) a first air pump having an input and an output;

(ii) a cartridge containing a desiccant and having an input and output with the input of the cartridge being connected to the output of said first air pump and providing a cartridge flow rate;

(iii) a second dividing means receiving said output of said cartridge and separating said cartridge flow rate into four paths respectively carrying fourth, fifth, sixth and seventh flow rates, said fourth flow rate being in fluid communication with one of said input ports of said ion mobility spectrometer arranged with said reagent source, said sixth flow rate being in fluid communication with one of said input ports of said ion mobility spectrometer not arranged with said reagent source, and said seventh flow rate being in fluid communication with said fourth port of the retainer having arranged herein the second permeable membrane; and (iv) a container housing said reagent source of said one of said ion mobility spectrometers and having an input and an output with the input of the container receiving the fifth flow rate and the output of the container being connected to the fourth port of the first retainer having arranged therein the first permeable membrane.

5. The portable system according to claim 4, further comprising a second air pump having an input and an output with the input receiving the outputs of said second ports of said first and second retainers and exhausting the flow of said first and second samples that do not pass through a respective one of said permeable membranes through the output of the second air pump.

6. The portable system according to claim 4, wherein said vapor receiving means further comprises:

(a) a first ionization chamber disposed in said first ion mobility spectrometer having an input and an output with the input being connected to said fourth flow rate and to said third port of said first retainer having said first permeable membrane therein, said first ionization chamber containing a first radioactive source; and (b) a second ionization chamber disposed in said second ion mobility spectrometer having an input and an output with the input being connected to said sixth flow rate of said third dividing means and to said third port of said second retainer having said second permeable membrane therein, said second ionization chamber containing a second radioactive source.

7. The portable system according to claim 6, wherein the first and second radioactive sources each comprises 100 microcuries of Americium—241 ($Am^{241}$).

8. The portable system according to claim 6, wherein said vapor receiving means provides corresponding representative electrical signals and further comprises:

(a) a first gate of said first ion mobility spectrometer having first and second electrodes and being connected to receive ion clusters from the output of said ionization chamber of said first ion mobility spectrometer, with the first electrode receiving a high voltage derived from a first high voltage source, said high voltage being about 24 volts higher than a second high voltage on a second electrode of said gate, the second high voltage being derived from said first high voltage source, with said high voltages on said first and second electrodes being made equal at first periodic intervals;

(b) a second gate of said second ion mobility spectrometer having first and second electrodes and being connected to receive ion clusters from the output of said ionization chamber of said second ion mobility spectrometer, with the first electrode receiving a high negative voltage derived from a second high voltage source, and said high negative voltage being about 24 volts higher than a second high negative voltage on a second electrode of said gate, the second high negative voltage being derived from said second high voltage source, with said high negative voltages on said electrodes thereof being made equal at second periodic intervals;

(c) a first drift region disposed in said first ion mobility spectrometer with entrance and exit portions with the entrance portion being connected to receive ion clusters from said first gate, said first drift region having evenly spaced apart first field electrodes which are connected to a first voltage divider producing respective voltages that decrease in a step-wise manner along a first drift axis of said first drift region, said first voltage divider being powered from said first high voltage source, so as to provide a predetermined voltage gradient between the entrance and exit portions of said first drift region;

(d) a second drift region disposed in said second ion mobility spectrometer with entrance and exit portions with the entrance portion being connected to receive ion clusters from said second gate, said second drift region having evenly spaced apart second field electrodes which are connected to a second voltage divider producing respective voltages that decrease in a step-wise manner along a second drift axis of said second drift region, said second voltage divider being powered from said second high voltage source, so as to provide a predetermined voltage gradient between the entrance and exit portions of said second drift region;

(e) a first collector of said first ion mobility spectrometer receiving ion clusters from the exit portion of said first drift region and producing a corresponding first electrical signal;

(f) a second collector of said second ion mobility spectrometer receiving ion clusters from the exit portion of said second drift region producing a corresponding second electrical signal;

(g) a first pole guard of said first drift region having a wire grid for focusing said ion clusters of said first drift region, thereby improving the resolving ability of said first electrical signal of said first collector; and (h) a second pole guard of said second drift region having a wire grid for focusing said ion clusters of said second drift region, thereby improving the resolving ability of said first electrical signal of said collector of said drift region of said first ion mobility spectrometer.

9. The portable system according to claim 8, wherein said first and second periodic intervals are about 30 ms.

10. The portable system according to claim 8, wherein each of said first and second high voltage sources is powered by a battery.

11. The portable system according to claim 8, wherein the first field electrodes include eleven (11) electrodes and wherein said first voltage divider produces eleven voltage steps that are sequentially and evenly decreased by 200 volts per step, with the first electrode being at 2000 volts and the eleventh electrode being at 0 volts so that the predetermined voltage difference between the entrance and exit portions of said first drift region is 2000 v.

12. The portable system according to claim 8, wherein the second field electrode include eleven (11) electrodes and wherein said second voltage divider produces eleven voltage steps that are sequentially and evenly increased by 200 volts per step, with the first electrode being at −2000 volts and the eleventh electrode being at 0 volts, so that the predetermined voltage difference between the entrance and exit portions of said second drift region is −2000 v.

13. The portable system according to claim 8, wherein the temperature of said housing is maintained at about 180° F. by a heater disposed in said housing.

14. The portable system according to claim 4, wherein said comparing means comprises:

(a) means for storing and accessing stored data corresponding to electrical signals representative of said predetermined chemical vapors;

(b) means for generating first and second digital signal data responsive to said representative electrical signals of said first and second ion mobility spectrometers; and (c) means for comparing said first and second digital signal data against the stored data and generating an alarm signal if a match exists therebetween.

15. A portable system enclosed in a unity housing for sampling the ambient of a selected environment for the presence of predetermined chemical vapors therein, the portable system comprising:

a sample filter having an upstream side fluidly coupled to the selected environment;

a retainer supporting first and second permeable membranes, which membranes divide the retainer into first, second, and third portions, wherein the second portion is bounded by the first and second permeable membranes;

a sample pump pneumatically coupled to the downstream side of the filter via the second portion of the retainer, the sample pump discharging to the selected environment;

a first ion mobility spectrometer (IMS) generating a first electrical signal;

a second IMS generating a second electrical signal;

a recirculation pump fluidly coupled to respective outlets of the first and second IMSs;

a recirculation filter disposed downstream of the recirculation pump;

a manifold disposed downstream of the recirculation filter, which manifold generates first and second recirculation flow rates;

a reagent source;

a controller which compares each of the first and second electrical signals against predetermined signals representative of the predetermined chemical vapors and generates an alarm signal if a match exists; and a power source for supplying electrical power to the sample pump, the first IMS, the second IMS, the recirculation pump, and the controller, wherein:

the power source is capable of being excited by a battery;

a first recirculation path operating at the first recirculation flow rate includes the first IMS, the recirculation pump, the recirculation filter, the manifold, the reagent source, and the first portion of the retainer, arranged in the stated order, one outlet of the first portion of the retainer being fluidly coupled to the input of the first IMS; and a second recirculation path operating at the second recirculation flow rate includes the second IMS, the recirculation pump, the recirculation filter, the manifold, and the third portion of the retainer, arranged in the stated order, one outlet of the third portion of the retainer being fluidly coupled to the input of the second IMS.

16. The portable system according to claim 15, wherein the portable system includes electromagnetic interference protection so as to permit detection of said predetermined chemical vapors in the presence of electromagnetic interference.

17. The portable system according to claim 15, wherein said portable system can be calibrated with respect to known chemical vapors so as to prevent the generation of said alarm in the presence of known interferents.

18. The portable system according to claim 15, wherein the first IMS and the second IMS each includes a radioactive source of 100 microcuries of Americium −241 ($Am^{241}$).

19. The portable system according to claim 15, wherein said controller comprises:

(a) means for storing and accessing stored data corresponding to electrical signals representative of said predetermined chemical vapors;

(b) means for generating first and second digital signal data responsive to the first and second electrical signals; and (c) means for comparing said first and second digital signal data with respect to the stored data and generating an alarm signal if a match exists therebetween.

20. The portable system according to claim 15, wherein the temperature of the housing is maintained at about 180° F. by a heater disposed in the housing.

* * * * *